United States Patent
Zeng et al.

(10) Patent No.: US 11,666,711 B2
(45) Date of Patent: Jun. 6, 2023

(54) PEN NEEDLE ASSEMBLY APPARATUS

(71) Applicant: Embecta Corp., Andover, MA (US)

(72) Inventors: Xi Zeng, Suzhou (CN); Huasheng Huang, Suzhou (CN); Wei Hu, Shanghai (CN); Junyu Zhou, Shanghai (CN)

(73) Assignee: Embecta Corp., Andover, MA (US)

( * ) Notice: Subject to any disclaimer, the term of this patent is extended or adjusted under 35 U.S.C. 154(b) by 190 days.

(21) Appl. No.: 16/957,640

(22) PCT Filed: Dec. 19, 2018

(86) PCT No.: PCT/US2018/066533
§ 371 (c)(1),
(2) Date: Jun. 24, 2020

(87) PCT Pub. No.: WO2019/133390
PCT Pub. Date: Jul. 4, 2019

(65) Prior Publication Data
US 2020/0324058 A1   Oct. 15, 2020

(30) Foreign Application Priority Data

Dec. 28, 2017  (CN) ........................ 2017/11456020.X
Dec. 28, 2017  (CN) ........................ 2017/21885567.7

(51) Int. Cl.
*A61M 5/34* (2006.01)
*A61M 5/32* (2006.01)

(52) U.S. Cl.
CPC .......... *A61M 5/343* (2013.01); *A61M 5/3205* (2013.01); *A61M 5/3295* (2013.01)

(58) Field of Classification Search
CPC .. A61M 5/343; A61M 5/3205; A61M 5/3295; A61M 5/3204; A61M 2005/004;
(Continued)

(56) References Cited

U.S. PATENT DOCUMENTS 5,829,589 A   11/1998  Nguyen et al.
5,873,462 A *  2/1999  Nguyen ................ A61M 5/002
                                                       206/534
(Continued)

FOREIGN PATENT DOCUMENTS

AU   2009202158 A1   12/2009
CN   102791309 A     11/2012
(Continued)

OTHER PUBLICATIONS

International Search Report dated Mar. 22, 2019, which issued in the corresponding PCT Patent Application PCT/US2018/066533.

*Primary Examiner* — Lauren P Farrar
*Assistant Examiner* — Hamza A Darb
(74) *Attorney, Agent, or Firm* — Greenberg Traurig, LLP; Roman Fayerberg; David J. Dykeman

(57) ABSTRACT

A pen needle assembly apparatus (60) includes a housing (30), a movable support (40) for supporting a pen needle (18), an ejector (80) for ejecting a used pen needle from the support, and an actuator (56). The support (40) is rotated relative to the housing (30) to index the pen needles to a position where the pen needle can be accessed and coupled to a delivery device (10). The used pen needle (18) is returned to the well (42) in the support and the support rotated toward the ejector (80) where the used pen needle is ejected to a compartment (50) in the housing for disposal. A cover (60) on the housing includes at least one opening (65) for accessing the pen needle when the support is rotated to position a pen needle relative to the opening in the cover.

22 Claims, 16 Drawing Sheets

(58) Field of Classification Search
CPC .......... A61M 2005/3208; A61M 5/002; A61M 5/008; A61M 5/001; A61B 50/362
See application file for complete search history.

(56) References Cited

U.S. PATENT DOCUMENTS

| | | |
|---|---|---|
| 6,923,319 B1 | 8/2005 | Erickson et al. |
| 2005/0056121 A1 | 3/2005 | Lyman |
| 2005/0269226 A1* | 12/2005 | Erickson ............. A61M 5/3205 206/363 |
| 2005/0269227 A1 | 12/2005 | Erickson et al. |
| 2006/0229562 A1 | 10/2006 | Marsh et al. |
| 2007/0149924 A1 | 6/2007 | Marsh |
| 2014/0027329 A1 | 1/2014 | Dasbach et al. |
| 2014/0332425 A1 | 11/2014 | Hofmann et al. |
| 2016/0166759 A1 | 6/2016 | Dasbach et al. |

FOREIGN PATENT DOCUMENTS

| | | |
|---|---|---|
| CN | 208770577 U | 4/2019 |
| EP | 1321157 A2 | 6/2003 |
| GB | 2459772 A | 11/2009 |
| JP | 2003000658 A | 1/2003 |
| JP | 2007-14615 A | 1/2007 |
| WO | 2005120611 A1 | 12/2005 |
| WO | 2009136193 A1 | 11/2009 |
| WO | 2011036491 A2 | 3/2011 |
| WO | 2017189171 A1 | 11/2017 |
| WO | 2018106680 A1 | 6/2018 |

* cited by examiner

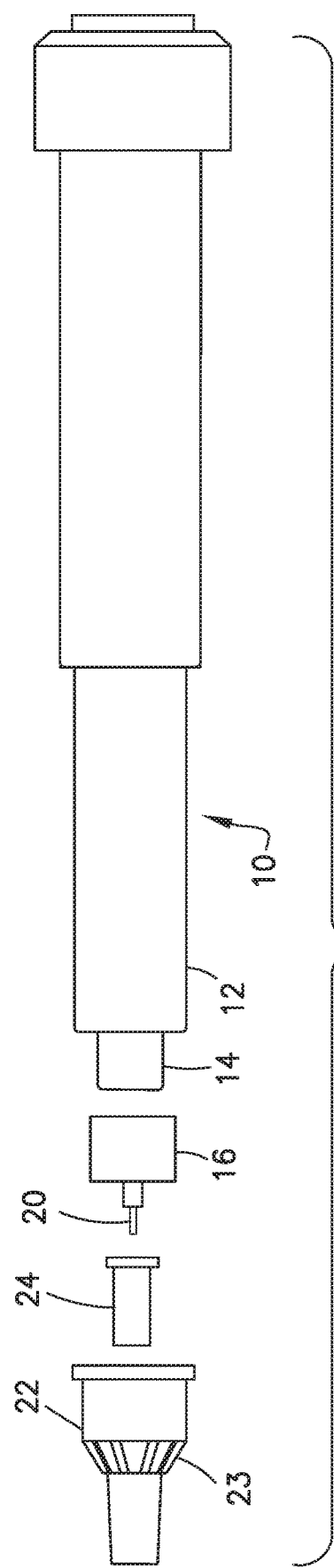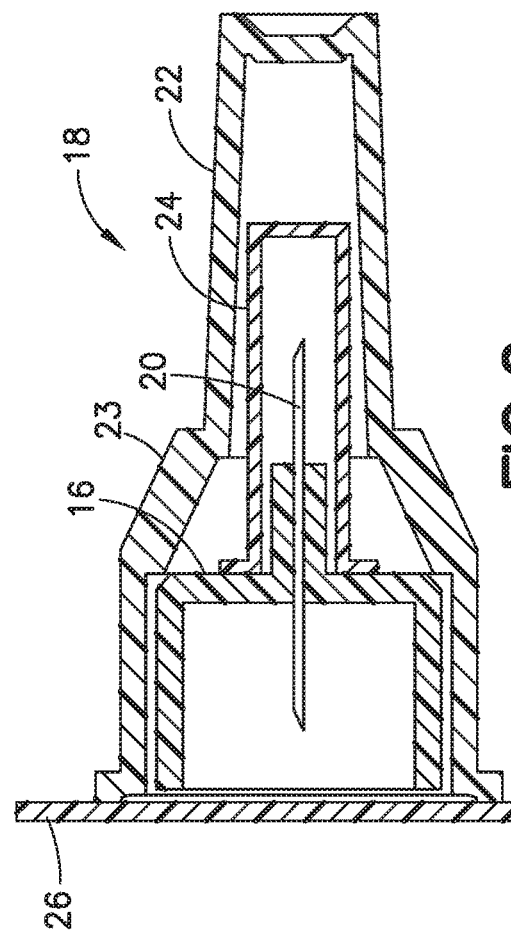

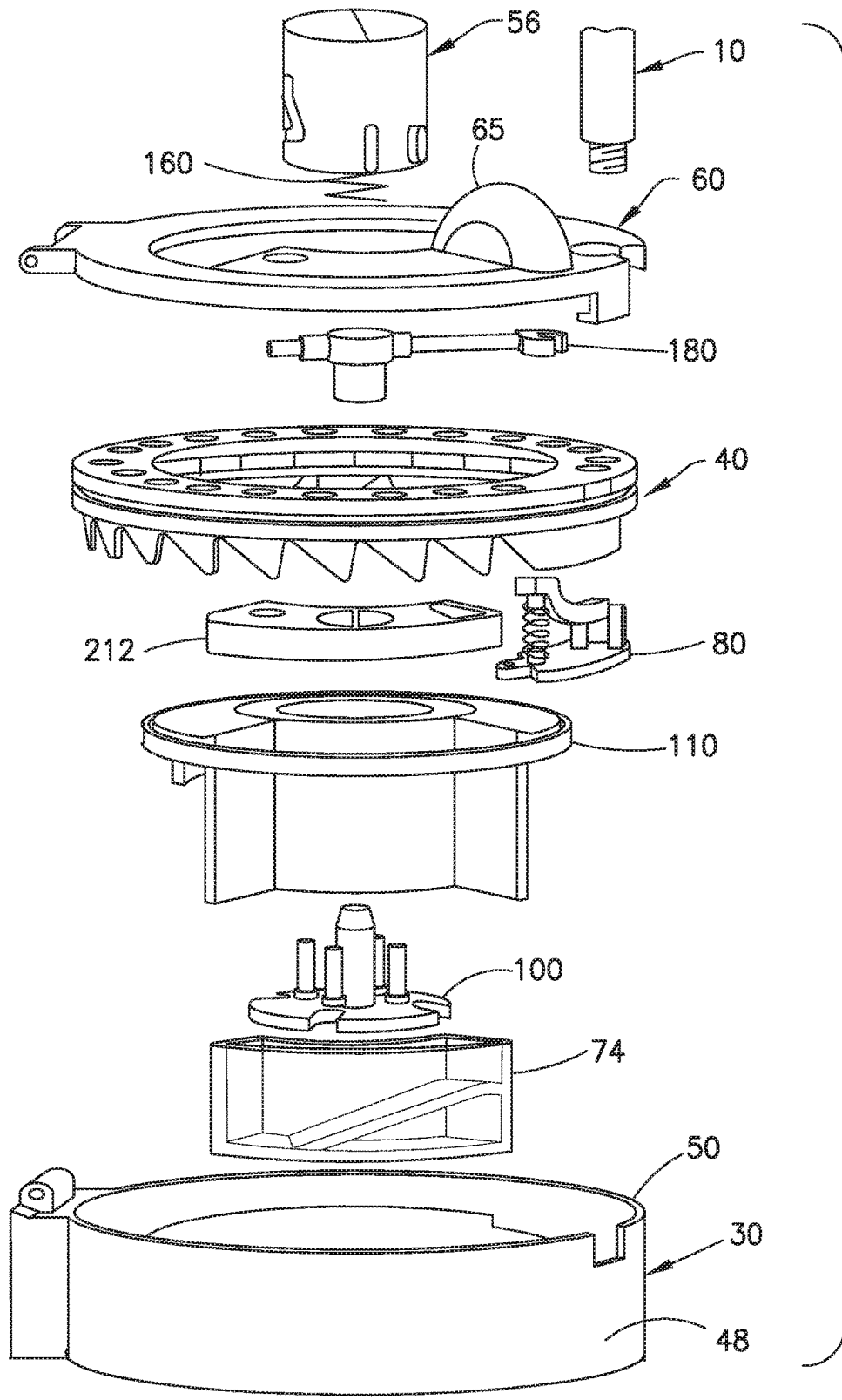

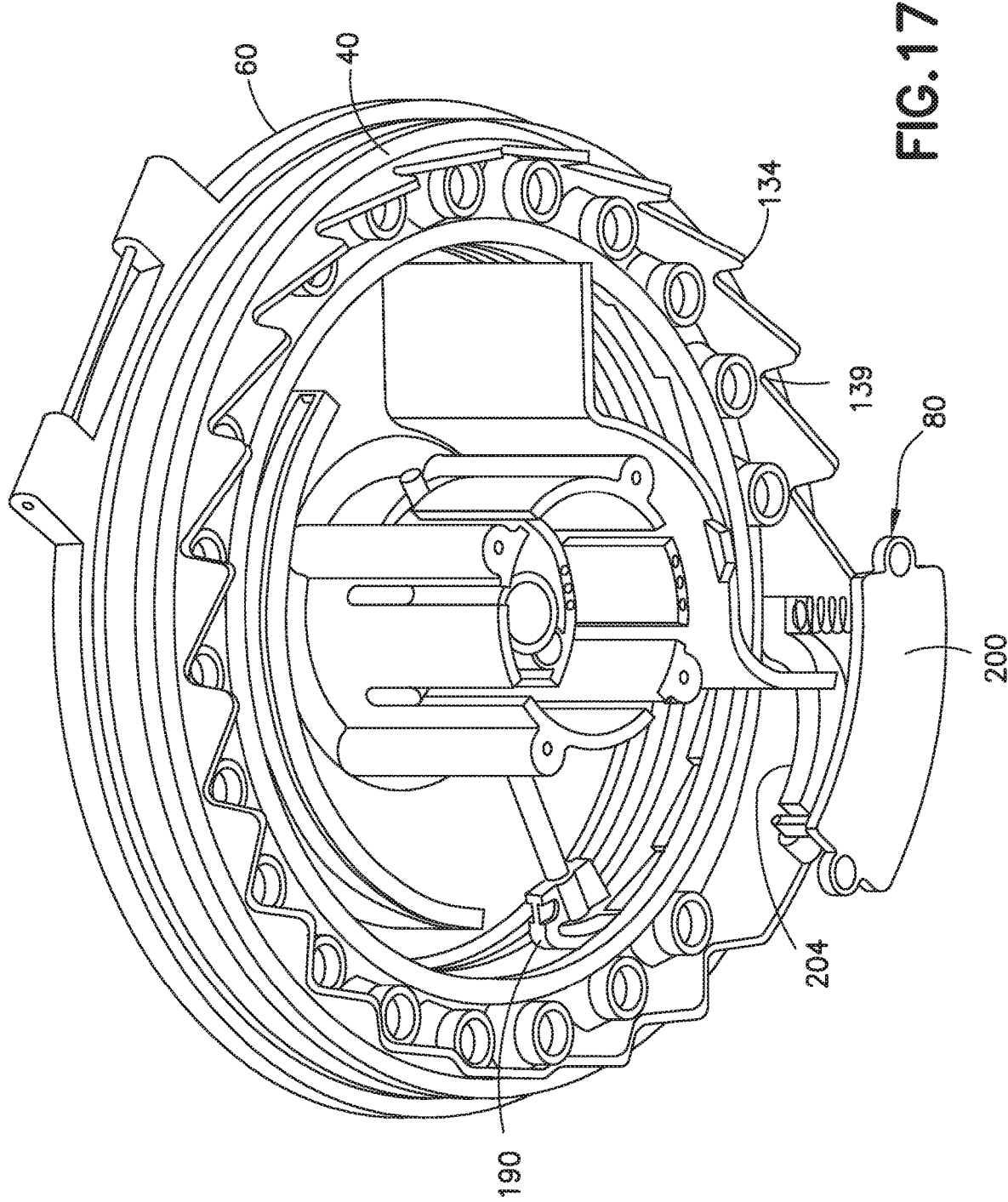

PEN NEEDLE ASSEMBLY APPARATUS

This application claims priority to Chinese Application No. 2017/21885567.7 filed Dec. 28, 2017 and Chinese Application No. 2017/11456020.X filed Dec. 28, 2017, which are hereby incorporated by reference in their entirety.

FIELD OF THE INVENTION

The present invention relates generally to a pen needle assembly apparatus and to an apparatus for attaching a pen needle assembly to a pen delivery device. The apparatus has a well or opening for retaining a needle hub with an inner shield before and after use to reduce the risk of inadvertent needle stick. The apparatus is able to move the used pen needle to a compartment or removable tray for disposal. The apparatus has a second well to receive the inner shield for separating the inner shield of the pen needle from the needle hub without the need to handle the inner shield.

BACKGROUND OF THE INVENTION insulin and other injectable medications are commonly delivered with drug delivery pens, whereby a disposable pen needle hub is attached to the pen to facilitate drug container access and allow fluid egress from the container through the needle into the patient.

Various pen needle delivery devices are known in the art for dispensing the substance to the patient. The delivery devices often use a disposable needle hub having a cannula or needle extending from a patient end of the hub for inserting into the patient. A non-patient end of the hub is coupled to the pen delivery device for delivering the substance to the patient.

The needle hub assembly is often packaged in a container containing several loose needle hubs. A needle hub is selected from the package and attached to the pen needle delivery device for injecting the patient and then removed to be discarded. The needle hub package includes an outer cover that encloses the needle hub and a removable seal that is peeled from the outer cover to open the cavity so that the needle hub can be removed. The needle hub can have threaded non-patient end that is threaded onto the delivery device. The delivery device with the attached needle hub is then removed from the outer cover. An inner needle shield is attached to the needle hub to cover the cannula until the device is ready for use. The shield is removed to expose the cannula for use to deliver the substance to the patient. After use, the needle hub can be inserted back into the outer cover to enclose the exposed cannula. The pen delivery device is separated from the needle hub leaving the needle hub within the outer cover.

The prior devices require the use of both hands to connect to and remove the needle hub from the delivery device. During the placement back into the outer cover, the cannula is exposed and provides an increased risk of accidental needle stick. The manual operation of holding the outer cover while positioning the spent needle hub and cannula into the cavity of the outer cover can be difficult without accidental needle stick.

Existing pen needle assemblies are disclosed in U.S. Patent Application Publication Nos. 2006/0229562 to Marsh et al. and 2007/01149924 to R. Marsh, the entire contents of both of which are hereby incorporated by reference.

Although the prior devices have been suitable for the intended use, there is a continuing need in the industry for improved packaging for a pen needle hub assembly.

SUMMARY OF THE INVENTION

The present invention is directed to a pen needle assembly apparatus and to an apparatus for receiving and supporting at least one pen needle assembly for attaching the pen needle assembly to a delivery device such as a delivery pen. In particular, the invention is directed to an apparatus for a pen needle assembly that can be used in a manner to reduce the risk of inadvertent needle stick while attaching and removing the pen needle assembly from the delivery pen and disposal of a used pen needle. The pen needle apparatus can include a mechanism for advancing a pend needle to a position where the pen needle can be coupled to a delivery pen and for advancing a used pen needle to a position where the used pen needle can be transferred to a storage tray or bin.

In one embodiment of the invention, the apparatus is provided with a support having an opening or well for a pen needle. Typically the support has a plurality of wells for received a pen needle. The pen needle includes an outer cover, a needle hub for supporting a cannula or needle, and an inner shield covering the cannula. A removable seal closes the open end of the outer cover that is removed before attaching the needle hub to the delivery pen. The apparatus retains and supports the pen needle assembly and the needle hub and cannula while attaching to a delivery pen or other delivery device. The apparatus is able to store a used needle hub and the outer cover for disposal.

The apparatus has a recess or well for receiving and retaining the inner shield of the pen needle that covers the cannula so that the inner shield can be removed from the needle hub without the operator handling the inner shield. The used needle hub can be inserted back into the outer cover and transferred to a compartment having a storage tray or internal sharps container for disposal. The inner shield can be discarded in the storage tray. An actuator moves the support and pen needles to a position for attaching to a delivery device such as a delivery pen. An ejector transfers the used pen needle from the respective well to a suitable tray, container or disposal bin, such as a sharps container.

In one embodiment, the inner shield can be inserted into an opening that forms a well in the apparatus to engage an extractor having a gripping member within the apparatus so that the inner shield is retained by a friction fit or interference fit. The needle hub and cannula can then be pulled away to separate the inner shield while the inner shield is retained in the well without the need for the user to handle the inner shield. The inner shield can be pushed past the gripping member to pass into a tray or cavity in the apparatus that forms a sharps container.

One aspect of the invention is to provide an apparatus for receiving and supporting a plurality of pen needles to attach the needle hub to the delivery device such as a delivery pen without the need for the user to handle the needle hub with the exposed cannula on the needle hub. The pen needle is positioned in the apparatus so that the delivery device can be attached to the non-patient end of the needle hub. An inner needle shield on the needle hub can then be inserted into an opening in the device to grip the inner shield by an extraction mechanism so that the inner shield can be separated from the needle hub without handling the inner shield. After use, the needle hub is positioned in the outer cover that is retained in an opening of the apparatus and disconnected from the delivery device where the apparatus retains the used needle hub and outer cover.

The apparatus includes a housing having an internal cavity for receiving and storing used pen needles and the associated components. The housing has an opening to access a pen needle so that the needle hub can be attached to the delivery pen. The used needle hub can be inserted back into the outer cover that is retained in the apparatus and separated from the delivery pen.

A pen needle apparatus in one aspect comprises a housing, a pen needle support, and an actuator. The housing has an inner cavity, a top end, and a bottom end. The pen needle support has a plurality of wells for receiving a pen needle. The support is movable within the housing by actuating the actuator to move the support and the respective pen needle to a location where pen needle is accessible by the delivery device. The support can then be moved to a position in the housing where the used pen needle is transferred to a compartment that can include a tray for disposal of the pen needles.

The features of the apparatus are provided by a pen needle assembly apparatus for receiving a pen needle, where the apparatus includes a housing, a movable support, and an actuator. The housing has an inner compartment for receiving a used pen needle for disposal. A support is provided in the housing where the support has a plurality of wells. Each of the wells is configured for receiving a pen needle. A cover is coupled to the housing and has an opening for accessing at least one of the pen needles stored in the support. An actuator is included for moving the support to a position where the pen needles are sequentially indexed to a position where the pen needles are accessible through the opening in the cover.

After use of the needle hub and cannula, the needle hub while attached to the delivery pen is inserted into the opening and into the outer cover where the needle hub can be gripped by a friction fit or interference fit to the outer cover so that the pen needle delivery device can be separated from the needle hub without the operator handling the needle hub thereby reducing the risk of inadvertent needle stick. The support for the pen needle can then be moved to a position where the used pen needle is ejected into a compartment for the used pen needles for disposal.

The features of the pen needle assembly apparatus are further attained by providing a housing having a top end, a rotatable support positioned in the housing, a cover, and an ejector. The support has a plurality of wells with a dimension for receiving a pen needle. The cover is coupled to the top end of the housing where the cover has an opening for accessing a pen needle assembly where the support can be rotated and indexed to a position to access each pen needle through the opening in the cover. The well can receive a used pen needle for disposal. The ejector ejects the used pen needle from the well into a compartment of the housing by rotation of the support relative to the housing.

In further embodiments, a method is provided for coupling the needle hub of a pen needle to a delivery device using a pen needle assembly apparatus. The apparatus has a pen needle housing with a rotatable support and an actuator for rotating the support. The support has a plurality of wells receiving a pen needle and the housing includes an ejector for ejecting the pen needle from the well after use. The method includes the steps of inserting the coupling end of the delivery device into a pen needle within a well and coupling to the open end of the needle hub. The delivery device with the needle hub attached is removed leaving the outer cover retained in the housing. The inner shield is inserted into an opening or well where the inner shield is gripped with sufficient force that the needle hub can be pulled free and separated from the inner shield to expose the cannula for use in delivering the substance to the patient.

After use, the needle hub is inserted into the outer cover that was retained in the well of the support and disconnected from the delivery device. The actuator is then actuated to rotate the support into engagement with the ejector where the used pen needle is ejected from the well to a compartment for disposal.

The Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which:

FIG. 1 is an exploded perspective view of a pen needle delivery device in one embodiment showing the pen needle assembly that includes a needle hub supporting a cannula, inner shield, and outer cover;

FIG. 2 is a cross-sectional view of the pen needle assembly;

FIG. 5 is an exploded view of the apparatus of FIG. 3;

FIG. 17 is a bottom perspective view of the support and ejector mechanism;

Throughout the drawings, like reference numbers will be understood to refer to like parts, components, and structures.

DETAILED DESCRIPTION OF THE EXEMPLARY EMBODIMENTS

Figure 4:
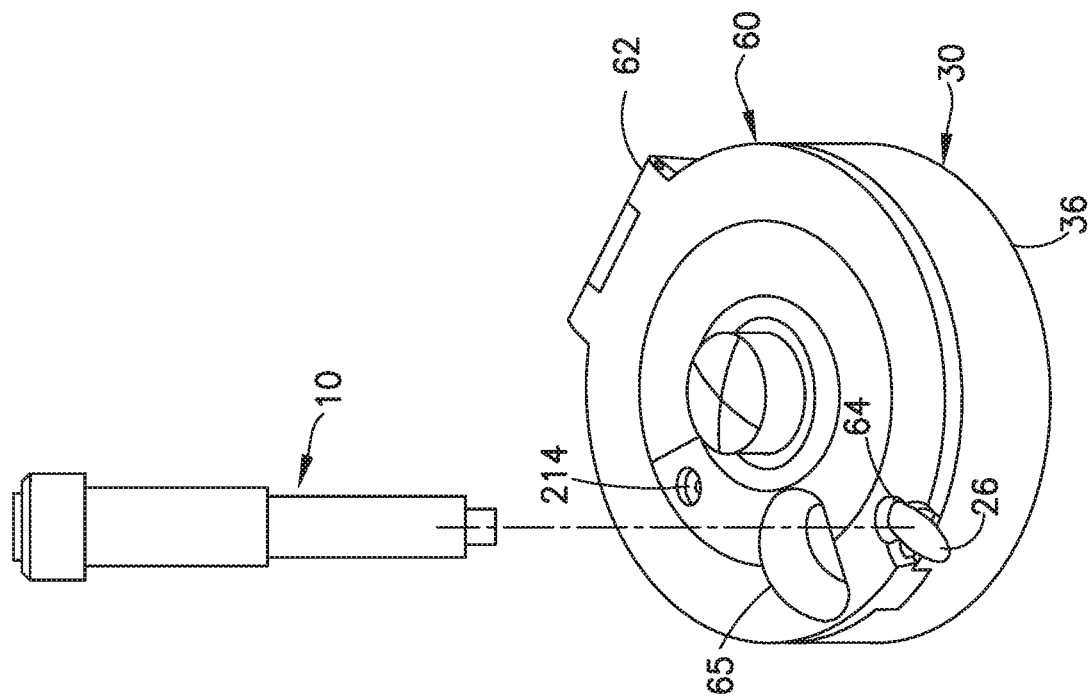
FIG. 4 is a right side perspective view of the apparatus of FIG. 3 showing a pen needle positioned in the opening of the cover.

A pen needle assembly apparatus for storing and supporting at least one and preferably a plurality of pen needles for use with a delivery device such as delivery pen. The apparatus receives a used needle hub where the used needle hub can be replaced in the device after use and discarded without handling the needle hub to reduce the risk of accidental needle stick.

Reference will now be made in detail to embodiments of the present invention, which are illustrated in the accompanying drawings, wherein like reference numerals refer to like elements throughout. The embodiments described herein exemplify, but do not limit, the present invention by referring to the drawings. The exemplary embodiments are presented in separate descriptions, although the individual features and construction of these embodiments can be combined in any number of ways to meet the therapeutic needs of the user.

It will be understood by one skilled in the art that this disclosure is not limited in its application to the details of construction and the arrangement of components set forth in the following description or illustrated in the drawings. The embodiments herein are capable o of being modified, practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not limited to physical or mechanical connections or couplings. Further, terms such as up, down, bottom, and top are relative, and are employed to aid illustration, but are not limiting.

The apparatus for the pen needle can enable the convenient and easy assembly and removal of the needle hub on the pen delivery device with reduced handling of the exposed needle cannula. The apparatus for the pen needles can be placed on a flat surface, such as a table, so that the delivery device such as delivery pen can be attached to the needle hub with one hand thereby reducing the risk of the needle stick by handling the needle hub with the exposed needle cannula.

The delivery device is shown as a delivery pen 10 in FIG. 1. The delivery pen typically comprises a dose knob/button, an outer sleeve 12, and a cap. A dose knob/button allows a user to set the dosage of medication to be injected. The outer sleeve 12 is gripped by the user when injecting medication. The cap is used by the user to securely hold the pen injector device 10 in a shirt pocket or other suitable location and provide cover/protection from accidental needle injury.

In standard delivery pens or pen needle delivery devices, the dosing and delivery mechanisms are all found within the outer sleeve 12 and is not described in greater detail here as they are understood by those knowledgeable of the prior art. A medicament cartridge is typically attached to a standard pen injector housing by known attachment means. The distal movement of a plunger or stopper within the medicament cartridge causes medication to be forced into the reservoir housing. The medicament cartridge is sealed by a septum and punctured by a septum penetrating needle cannula located within a reservoir or housing. Reservoir housing is preferably screwed onto the medicament cartridge although other attachment means can be used. The pen needle delivery device can be a standard pen delivery device known in the industry so that the pen needle delivery device is not shown in detail. The pen needle assembly 18 as shown in FIG. 2 includes a needle hub 16 supporting a cannula 20, an outer cover 22, and an inner shield 24. A protective seal 26 is attached to the open end of the outer cover as shown in FIG. 2 to enclose the needle hub and cannula to maintain a clean and sterile condition. The seal 26 can be a label or other closure member that can be easily peeled from the outer cover to access the needle hub during use.

The pen needle delivery device 10 is connected to the needle hub 16 shown in FIG. 1 that has a connecting non-patient end with internal threads that screw onto a threaded end 18 of the delivery device 10. The needle cannula 20 extends from the patient end of the needle hub 16 for delivering the substance to the patient. The outer cover 22 can be provided to cover the needle cannula to protect the patient from accidental needle stick before and after use. The outer cover 22 includes ribs 23 to assist in gripping the outer cover during use. The inner shield 24 is provided over a post extending from the end of the needle hub 16 to enclose the cannula. During use, the needle hub 16 is connected to the pen delivery device and the inner shield is removed. After use, the outer cover is generally placed back on needle hub to cover the needle cannula. The needle hub with the cover is then removed from the pen needle delivery device and discarded.

The apparatus in one embodiment is configured for receiving and supporting at least one pen needle, and typically a plurality of pen needles in a position where the delivery device can be coupled to the needle hub for use for injecting the substance to the patient without the need for the user to handle the needle hub with the exposed cannula. The used needle hub and cannula can then be positioned back into the outer cover that is retained in the device and separated from the delivery device. The used outer cover and needle hub and the inner shield are transferred to a compartment in the apparatus for disposal.

Figure 3:
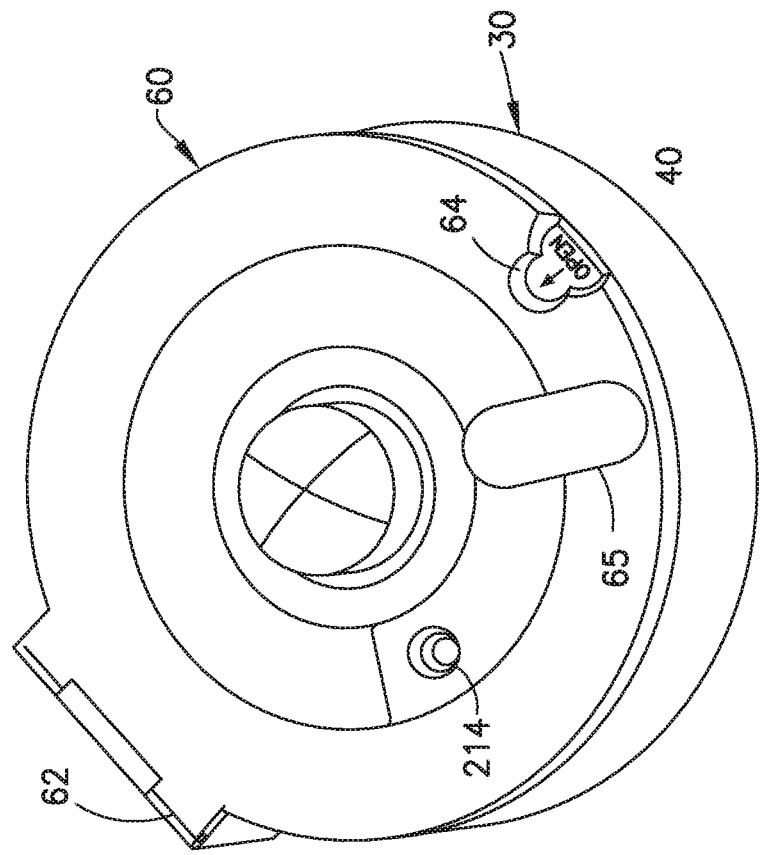
FIG. 3 is a left side perspective view of the pen needle assembly apparatus in one embodiment.
Figure 6:
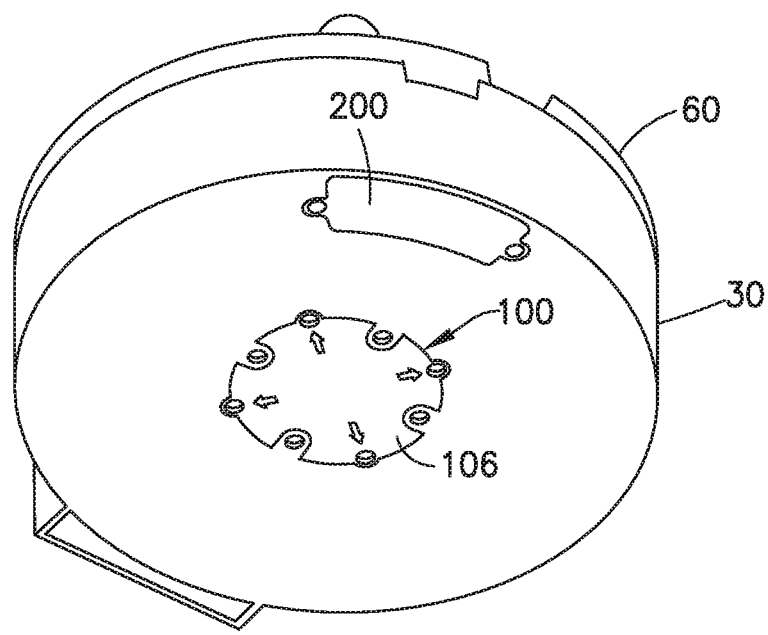
FIG. 6 is a bottom perspective view of the apparatus of FIG. 3.

In one embodiment the apparatus is configured for receiving a pen needle for coupling the pen needle hub 16 to the delivery pen and for separating the pen needle hub from the delivery pen after use. In one embodiment, the apparatus includes a housing 30 and a support 40 for retaining the plurality of pen needles. The housing 30 as shown in FIG. 3 and FIG. 4 has a side wall 48, a top end 34, and a bottom end 36. Bottom end 36 as shown in FIG. 6 has a bottom face that can include a non-slip surface. The nonslip surface can be molded directly onto the bottom face or can be a nonslip material, such as an elastomeric material, applied to the bottom surface to retain the housing in a stable position during use on a table or other flat surface.

Figure 7:
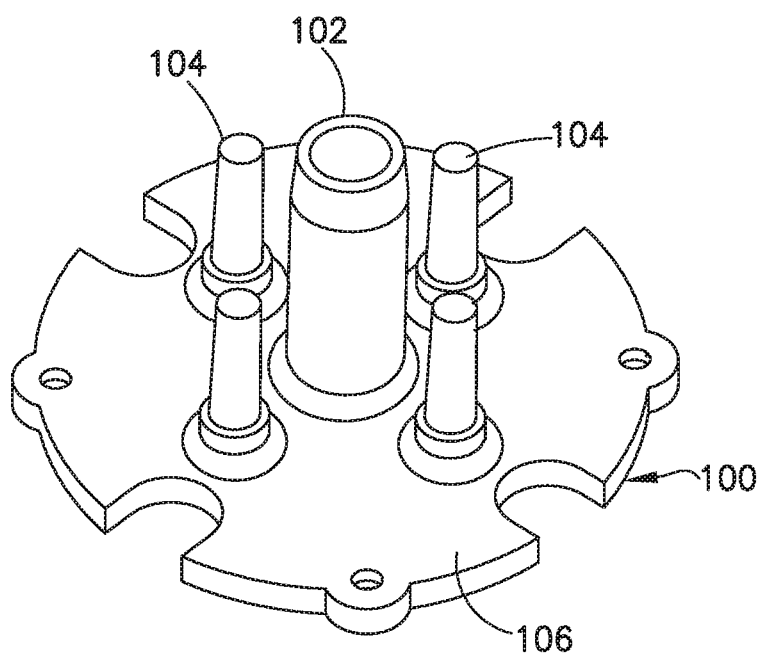
FIG. 7 is a top perspective view of the base member of the apparatus.

As shown in FIG. 6, the housing 30 has a bottom wall with an opening that receives a base 100 as shown in FIG. 5 and FIG. 7 for supporting the movable components of the assembly. The base 100 has a bottom wall 106 with a configuration for coupling to the bottom wall of the housing 30 as shown in FIG. 6. A center post 102 extends upwardly from the bottom wall 106 of the base 100 and is centrally located in the housing 30. A plurality of guide pins 104 extend from the base around the center post 102 and have an axial length less than the axial length of the center post 102.

Figure 8:
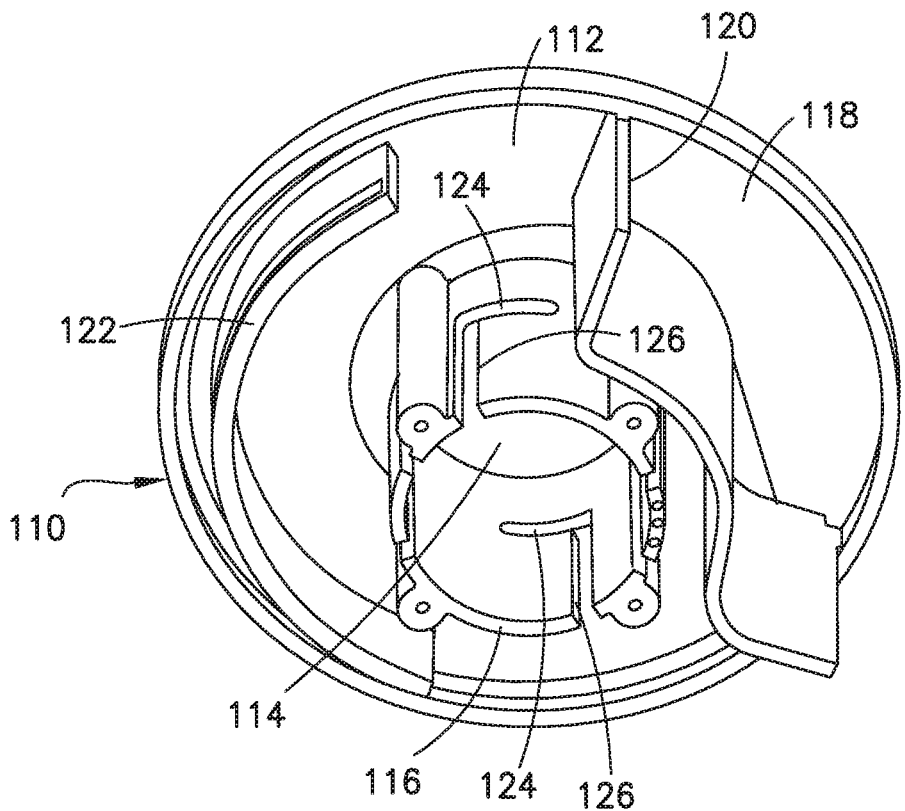
FIG. 8 is a bottom perspective view of the inner support of the apparatus.

An inner support 110 shown in FIG. 8 is attached to the base 100 and the bottom wall of the housing 30. The inner support 110 has a top wall 112 and a central opening 114 formed by a substantially cylindrical wall 116 spaced inwardly from the outer peripheral edge of the top wall 112. The central opening 114 defines a passage with a dimension for receiving the center post 102 and guide pins 104 of the base 100 and the actuator 56. The top wall 112 has an opening 118 formed by a side wall 120 for receiving a tray 94 for storing used pen needles. A guide rail 122 extends around a portion of the peripheral edge on the inner face of the top wall 112 for guiding the support 40. In the embodiment shown, the guide rail 122 is positioned opposite the side wall 120 and spaced inwardly from the peripheral edge.

The inner cylindrical wall 116 has a top end integrally formed with the top wall 112 and a bottom end for coupling to the bottom wall of the housing 30 and the base 100. As shown, the cylindrical wall 116 has a slot 124 oriented in a plane perpendicular to a longitudinal axis and extends in a circumferential direction around the wall 116. In the embodiment shown, two slots 124 are formed on opposite sides of the cylindrical wall 116 and include a longitudinal leg portion 126 for accessing the slot 124.

A support 40 forming a supporting ring or carousel is provided for supporting a plurality of pen needles 18 as shown in FIGS. 5 and 9-11. The support 40 in one embodiment has a top surface 130 with a plurality of wells 42 where each well has a shape and dimension configured for supporting and receiving a pen needle 18. The support 40 can have a suitable shape that is received in the housing 30. In one embodiment, the support 40 is movable for rotating to a number of angular positions for sequentially allowing access to each of the pen needles 18 for use by the patient when the pen needles 18 align with an opening 64 in the cover 60. The support 40 is shown having a circular, ring-like shape that is mounted in the housing 40 for rotating about a center axis although other shapes can be used.

Figure 15:
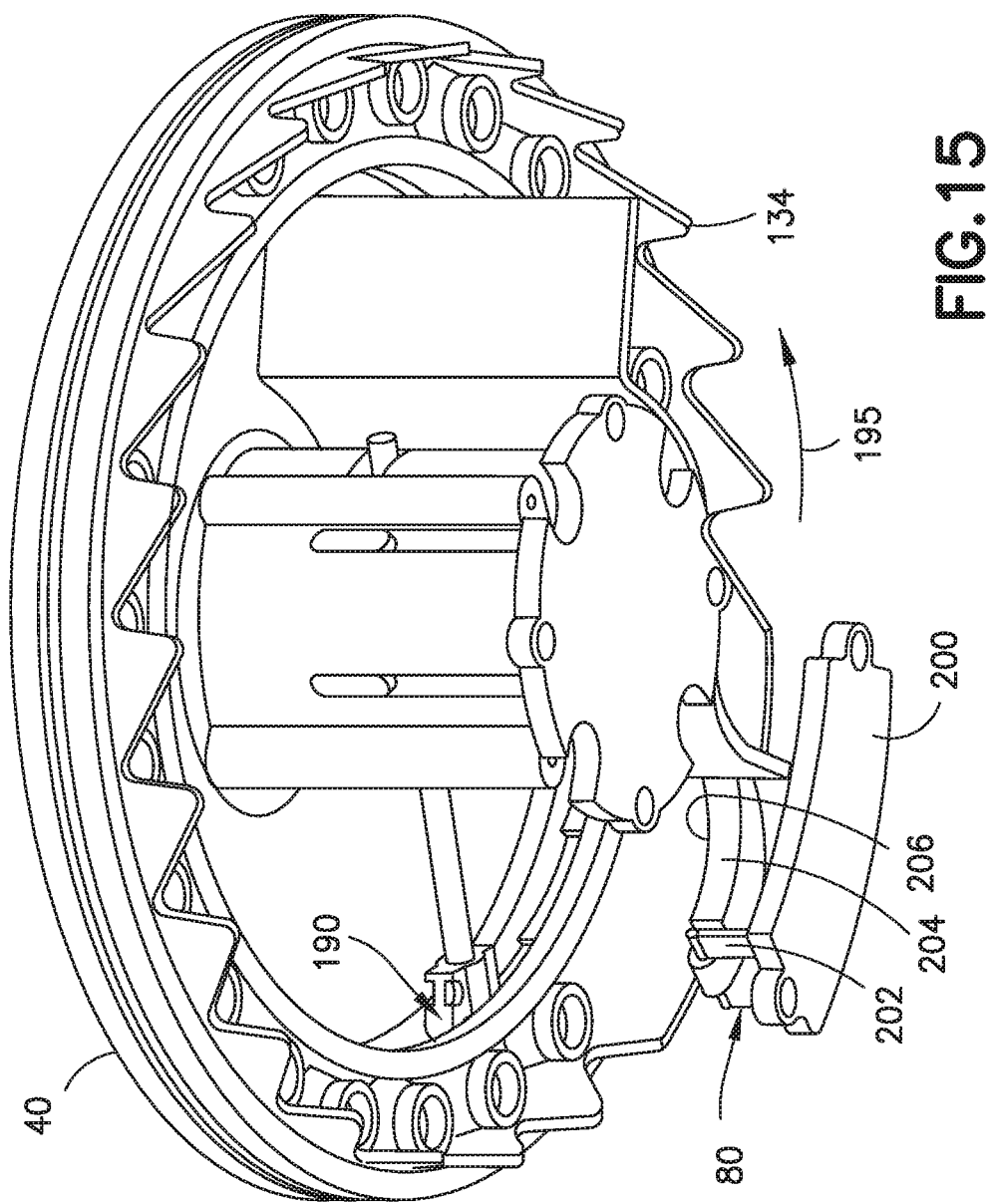
FIG. 15 is bottom perspective view of the support and ratcheting mechanism.

The wells 42 in the support 40 are defined by an open top end having a dimension for receiving the pen needle 18 so that the non-patient end of the pen needle and needle hub are oriented at the top end of the well 42. The wells 42 are formed by a circular side wall 44 having an open bottom 46 as shown in FIG. 11. The side walls 44 are tapered for complementing the shape of the outer cover 22 of the pen needle 28 and have an axial length less than the axial length of the outer cover so that the outer cover projects through the opening in the open bottom end 46 as shown in FIG. 10 and FIG. 15. For purposes of illustration, the pen needles are not shown installed in the well of the support in each of the figures although it will be understood that each of the wells can be loaded with a new pen needle before use. The inner surface of the side wall include at least one rib or recess shown in FIG. 9 that is able to engage the ribs 23 on the outer surface of the outer cover 22 to resist rotation of the outer cover 22 within the well 42.

Figure 9:
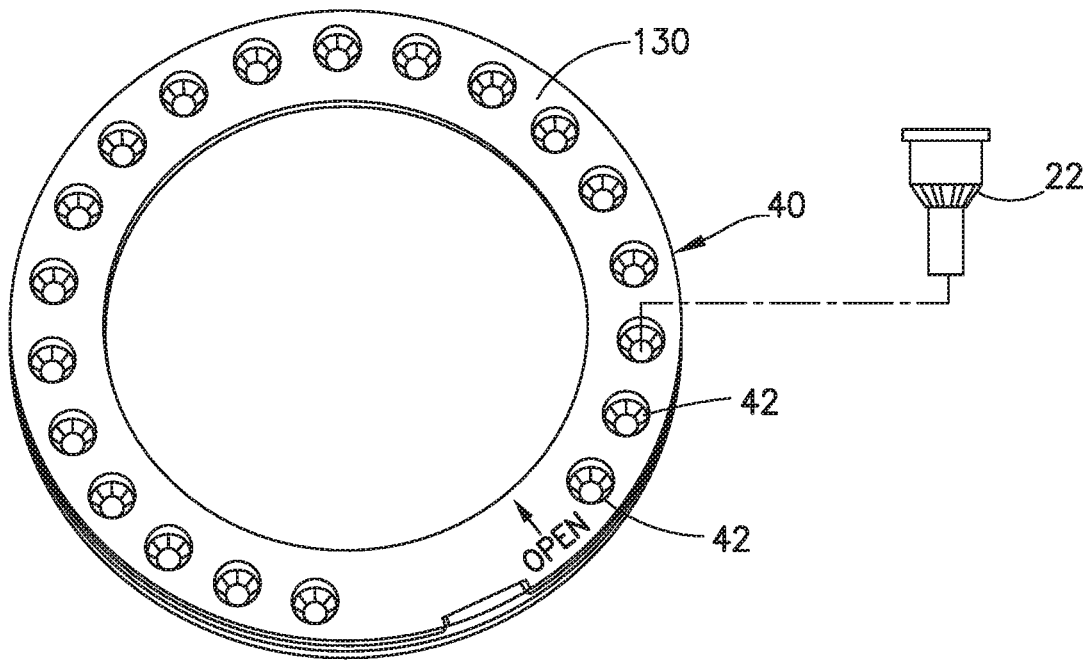
FIG. 9 is a top perspective view of the pen needle support ring.
Figure 10:
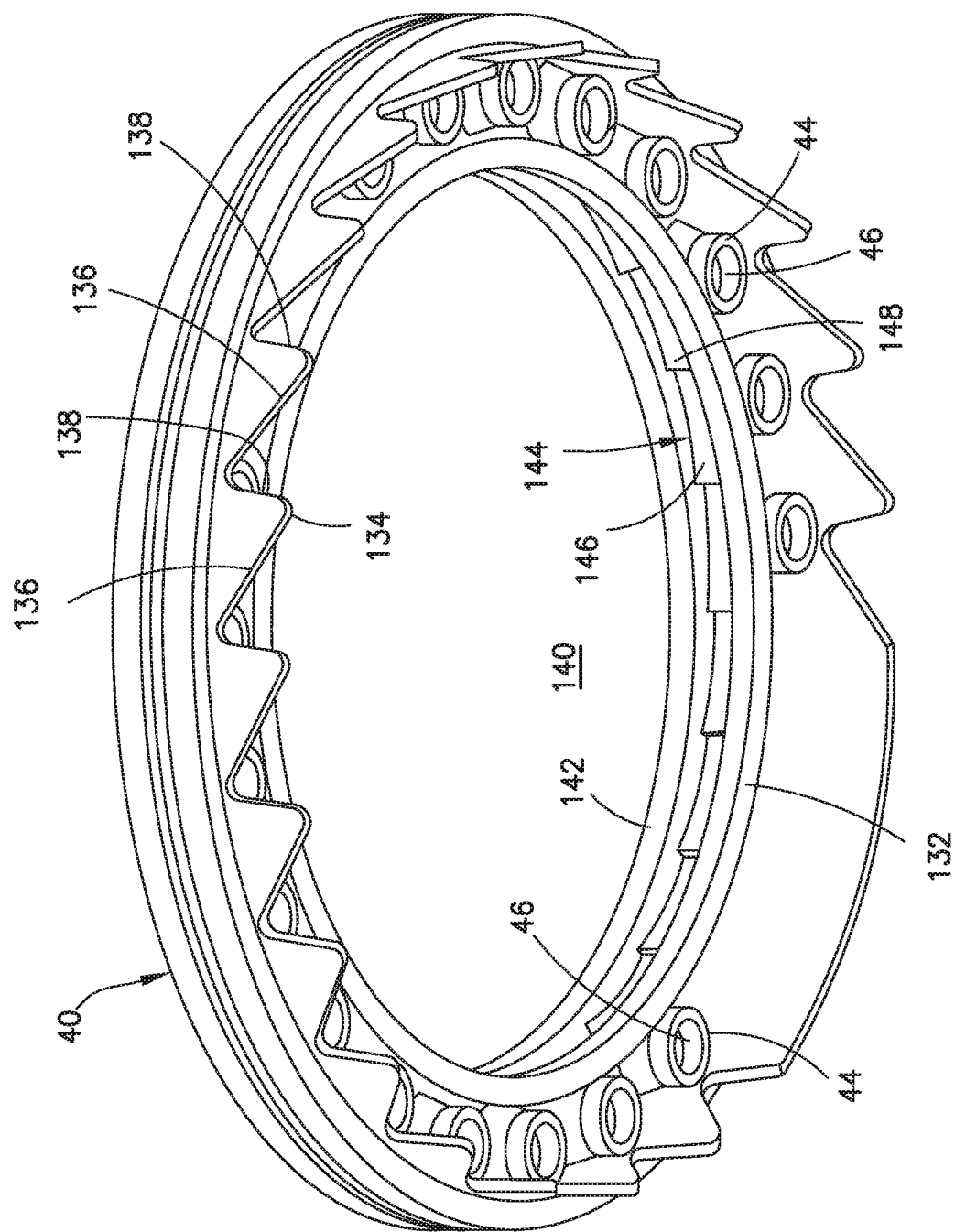
FIG. 10 is a bottom perspective view of the support of FIG. 9.
Figure 11:
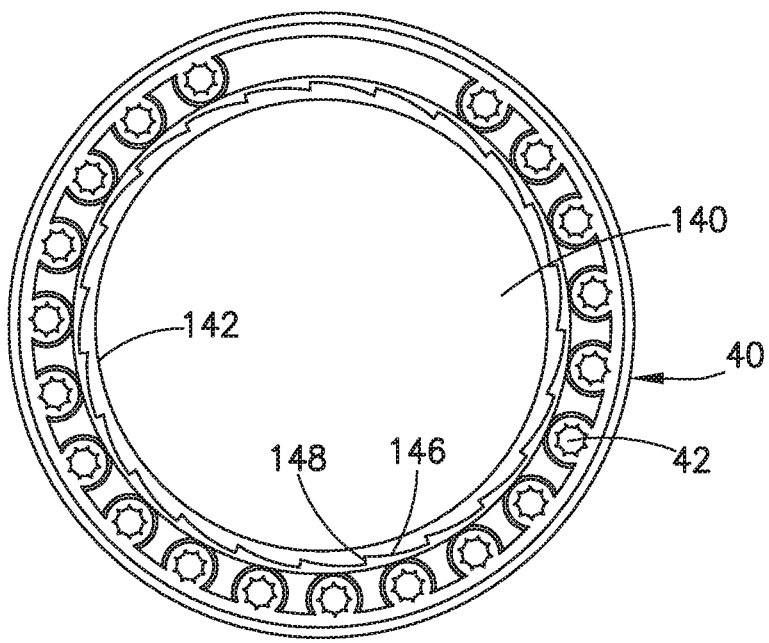
FIG. 11 is a bottom view of the support of FIG. 9.

In the embodiment shown in FIGS. 9-11, the support 40 is in the form of a ring having a top face 130 with openings formed by the well 42 and spaced around the circumference of the support 40. A bottom side 132 of the support 40 includes the side wall 44 of the respective well 42 as shown in FIG. 10. A plurality of angled teeth 134 are provided around the peripheral edge of the support 40 and project from the bottom side in an axial direction as shown in FIG. 10. The teeth 134 form a ratchet mechanism for allowing the support to rotate in one direction relative to the housing 30 and to operate the ejector mechanism 80. The teeth 134 are spaced apart around the peripheral edge and include an inclined face 136 and a vertical face 138.

The support 40 as shown in FIG. 10 has a central opening 140 forming inner annular surface 142. A plurality of ratcheting teeth 144 project radially inward from the inner annular surface 142 as shown in FIGS. 10 and 11. The ratcheting teeth 144 have an inclined surface 146 and a vertical surface 148 for cooperating with a rotator for rotating the support with respect to the housing.

An actuator 56 is connected to the housing for operatively connecting to the support 40 for moving and indexing the support 40 to a position where the pen needles 18 can be accessed and connected to a delivery pen as shown in FIG. 4. The actuator 56 in the embodiment shown moves in a linear direction with respect to the housing 30 and support 40. The actuator 56 can be in the form of a button that is manually depressed to cause the support 40 to rotate relative to the housing 30. In one embodiment, the actuator 56 moves in a linear up and down direction relative to the housing 30. In other embodiments, the actuator 56 can be located in other suitable locations.

The actuator 56 in the embodiment shown forms a button that is manually pushed down by the user to rotate the support 40 and index and advance a new pen needle into a position with respect to the cover 60 where the pen needle can be coupled to the delivery pen. The actuator 56 shown in FIG. 12 has a cylindrical side wall 150 with a top wall 152 and an open bottom end 154. The actuator 56 has an outer dimension and configuration to slide within the central opening 114 of the inner support 110 and in an opening in the cover 60. Outwardly extending lugs 156 project from the outer surface of the side wall 150 and are positioned at the open bottom end 154. In the embodiment shown, four lugs 156 are provided that slide within slots 158 formed in the cylindrical side wall 116 of the inner support 110. The lugs 156 cooperate with the inner support 110 to enable the actuator 56 to slide in an up and down linear direction and resist rotation with respect to the support 100 and the housing 30. A spring 160 is typically provided between the actuator 56 and the bottom wall of the housing or the base 100 to bias the actuator 56 to an extended upper position with respect to the housing 30 as shown in FIG. 3. The bottom end 154 of the actuator 56 can be provided with a plurality of cylindrical guides having an axial passage 155 forming guide holes for receiving a respective guide pin 104 on the base 100 for sliding the actuator in a linear direction.

Figure 12:
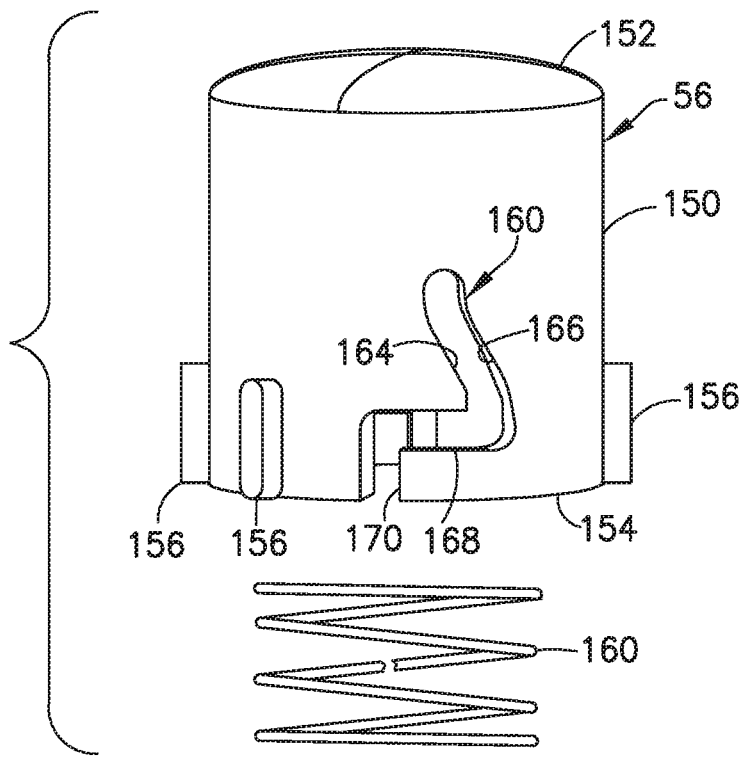
FIG. 12 is a front view of the actuator.
Figure 13:
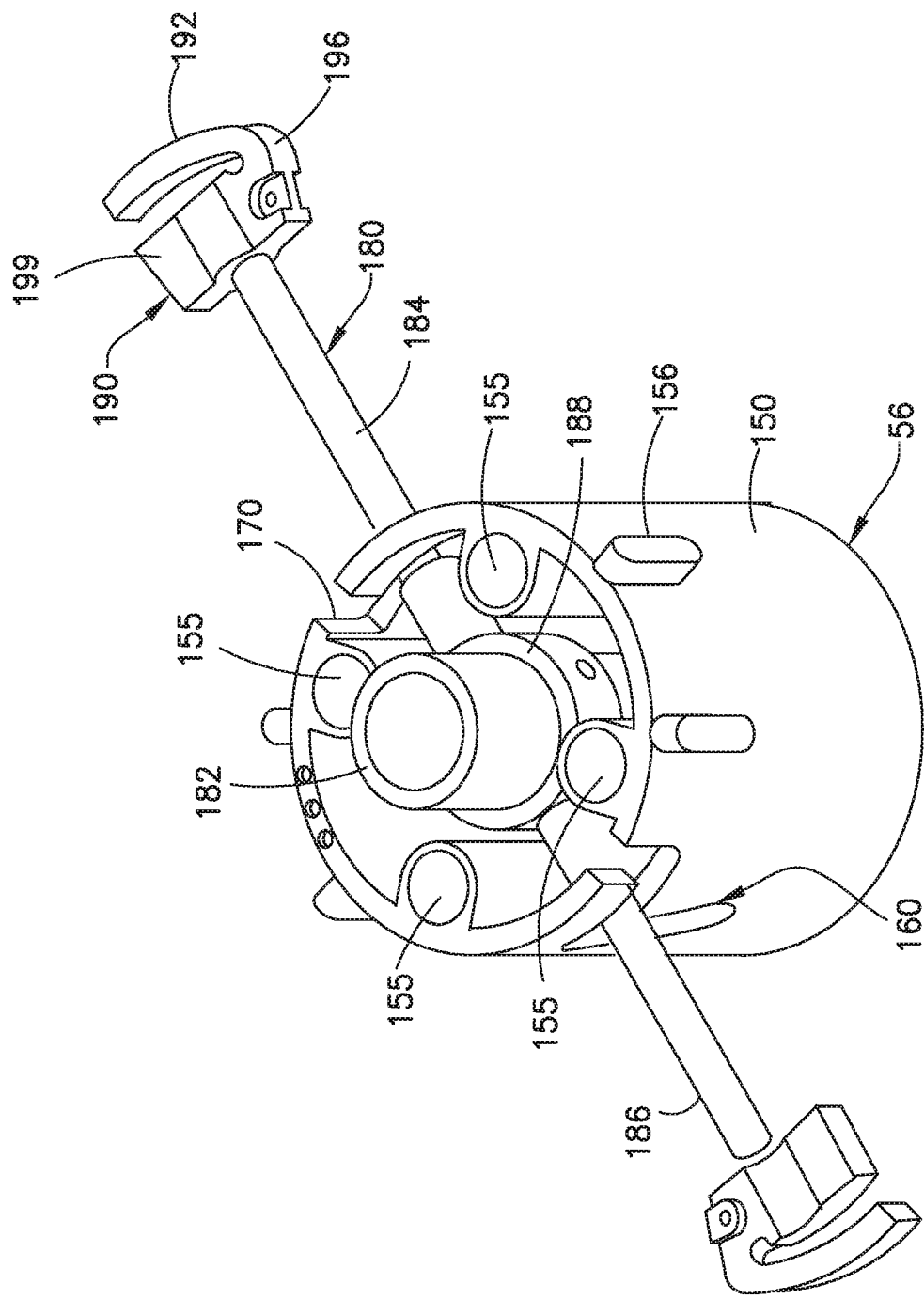
FIG. 13 is a bottom perspective view of the actuator shoving the ratcheting mechanism.

Referring to FIGS. 12 and 13, the side wall 150 of the actuator 56 includes a slot 162 forming a cam surface. The slot 162 has a first portion extending at an incline relative to the longitudinal axis of the actuator 56. The inclined section forms inclined cam surfaces 164 and 166. In the embodiment shown, an open horizontal leg portion 168 extends in a circumferential direction from the bottom end of the slot 158. A notch 170 is formed at one end of the leg for accessing the slot 162.

Figure 14:
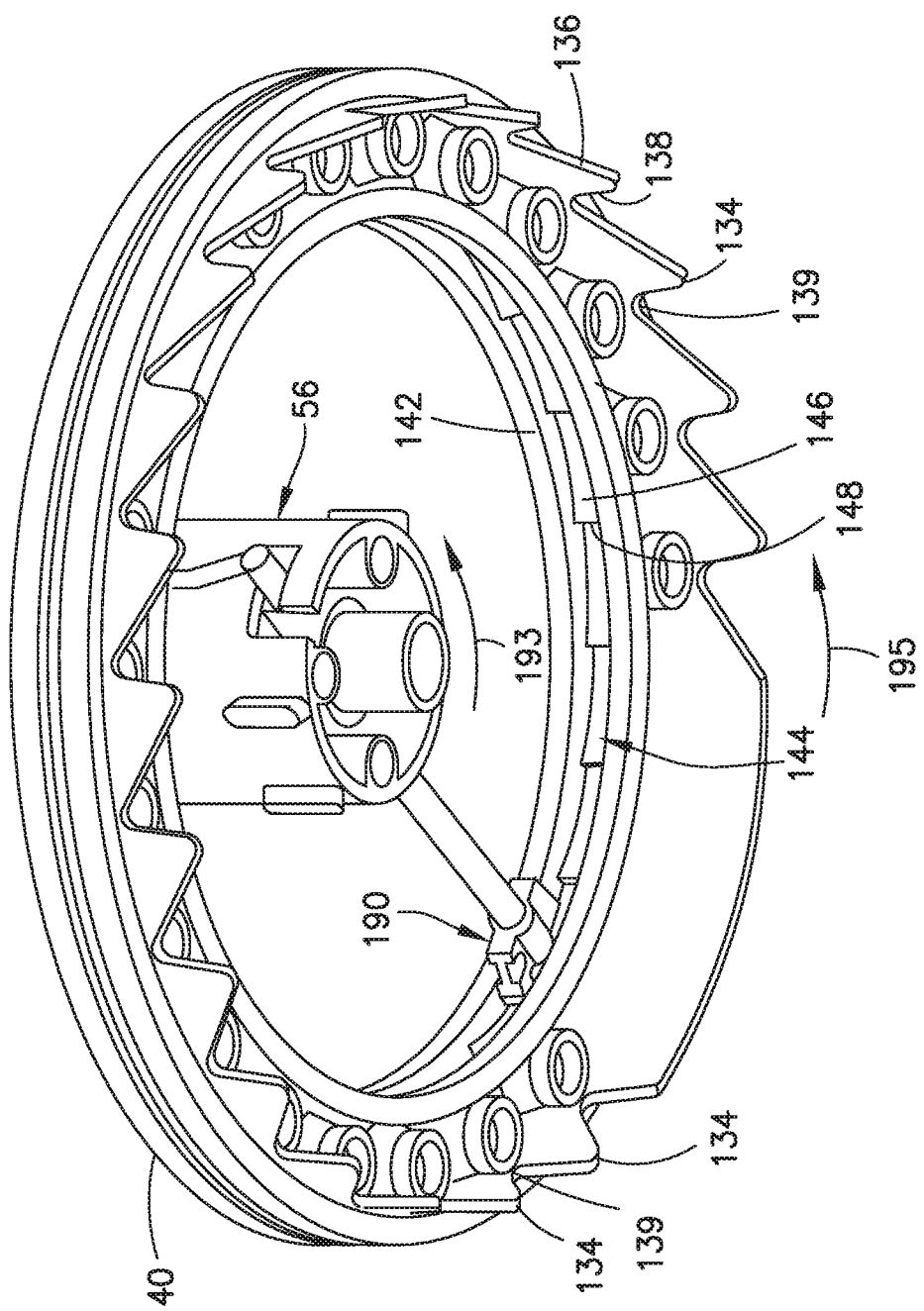
FIG. 14 is bottom perspective view of the support and ratcheting mechanism without the base member.

A rotator 180 is operatively connected to the actuator 56 as shown in FIGS. 13-15 for connecting the actuator 56 to the support 40 and rotating the support with respect to the housing. The rotator 180 in the embodiment shown has a cylindrical collar 182 that is rotatable on the central post 102. A first rod 184 extends from a first side of the ring 188 on the collar 182 and a second rod 186 extends from a second side of the ring 188 of the collar 182. As shown in FIG. 13, the rods 184 and 186 are received in the slots 162 and are coupled to the actuator 56. In one embodiment a spring 160, such as a coil spring, is provided on the post 102 to bias the actuator 56 in a an upward position.

The first rod 184 of the rotator 180 extends from the side wall 150 of the actuator a distance to engage the teeth 144 on the inner annular surface 142 of the support 40. As shown in FIG. 13, the distal end of the first rod 184 includes a ratchet member 190 for engaging the ratchet teeth 134 on the inner annular surface of the support 40. The ratchet 190 includes a flexible leg forming a pawl 192 connected to a body 194 by a flexible hinge portion 196 to bias the leg 192 radially outward from the actuator 56 into contact with the teeth 134 of the support 30. In the embodiment shown, the first rod 184 and second rod 186 include a ratchet 190. In other embodiments, one of the legs may not include a ratchet and pawl for engaging the teeth on the annular inner surface of the support. For ease of illustration, the ratchet and pawl on the second rod are not shown in each of the figures.

As shown in FIGS. 14 and 15 the linear movement of the actuator 56 causes the first rod 184 and the second rod 188 to rotate in a forward direction indicated by arrow 193 by engagement with the inclined cam surfaces 136 so that the distal end of the flexible leg 194 engages the respective tooth 134 on the inner annular surface of the support 40 to rotate the support 40 in the direction of arrow 195. The spring 160 biases the actuator 56 back to the original position. The upward movement of the actuator 56 causes the flexible leg 192 to move back to the original position and slide over the respective tooth in a direction opposite the arrow 193 to engage the next adjacent tooth 148 for advancing the support 40 with each pressing of the actuator 56.

A cover 60 is provided on the housing 30 to enclose the support 40 and the pen needles 18 until ready for use. The cover, in the embodiment shown is connected to the housing 30 by a hinge 62 although other mechanisms can be used to attach the cover to the housing. As shown in FIG. 3, the cover 60 includes at least one opening 64 for accessing a pen needle 18 when the pen needle is advanced to the opening 64. The opening 64 can have a generally U-shape with a dimension where the needle hub can be removed from the respective pen needle in the well 42 of the support 40. In one embodiment, the opening 64 has a dimension less than an outer dimension of the outer cover 22 of the pen needle 18 so that the outer cover 22 is retained in the well of the support 40 while allowing the needle hub to be removed. The actuator 56 is able to rotate and index the support 40 to bring a pen needle 18 into the opening 64 in the cover with each depression of the actuator 56.

As shown in the embodiment of FIG. 3, the cover 60 includes a dome-shaped projecting portion 65 projecting from a top surface of the cover next to or adjacent the opening 62. The projecting portion 65 forms a recess 66 in the bottom surface of the cover 60 shown in FIG. 21. The recess 66 has a first end 68 overlying the support 40 and a second end 70 extending inwardly from the inner wall 52 of the housing 30 and where the recess 66 has a dimension to receive the pen needle 18. A compartment 72 is provided in the housing having a storage tray 74 or bin for receiving used pen needles 18.

Referring to FIG. 16-19, an ejector 80 is provided in the housing 30 for ejecting a used pen needle 18 from the respective well 42 by rotation of the support 40 relative to the housing 30 and ejector 80. The ejector in one embodiment includes a base 200 shown in FIG. 16 that is mounted in an opening in the bottom wall of the housing 30 as shown in FIG. 6. A vertical support 202 extends from the base 20 and supports a pivoting arm 204. The arm 204 forms an inclined member having an inclined surface 206. The arm 204 is biased away from the base 200 by a spring 207 so that the arm 204 pivots about a pivot pin 209 relative to the support 202. The arm 204 has a first end 208 and is positioned for contacting the used pen needle projecting from the well 42 through bottom face of the support 40 as shown in FIG. 15. The arm 204 has a shape and dimension for contacting the distal end of outer cover 22 projecting from the bottom end of the respective well 42 when the support 40 rotates the pen needle into engagement with the ejector 80. The ejector 80 is attached to the housing 30 and is typically fixed to the housing below the support 40. As shown in the drawings, the cover 60 is oriented with respect to the housing 30 so that the opening 64 in the cover 60 is next to or adjacent the ejector 80 and the recess 66 is oriented at the end of the inclined surface 206 of the ejector 80.

Figure 16:
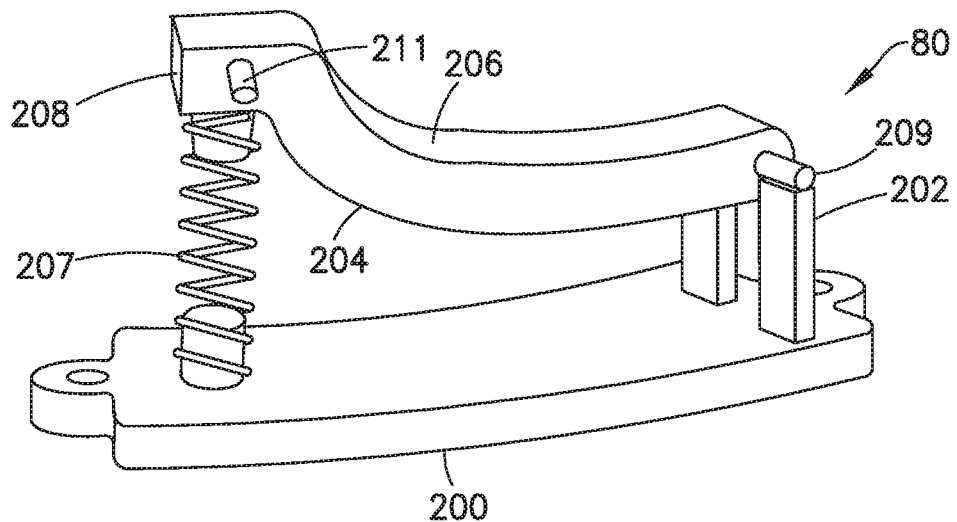
FIG. 16 is a perspective view of the pen needle ejector.
Figure 18:
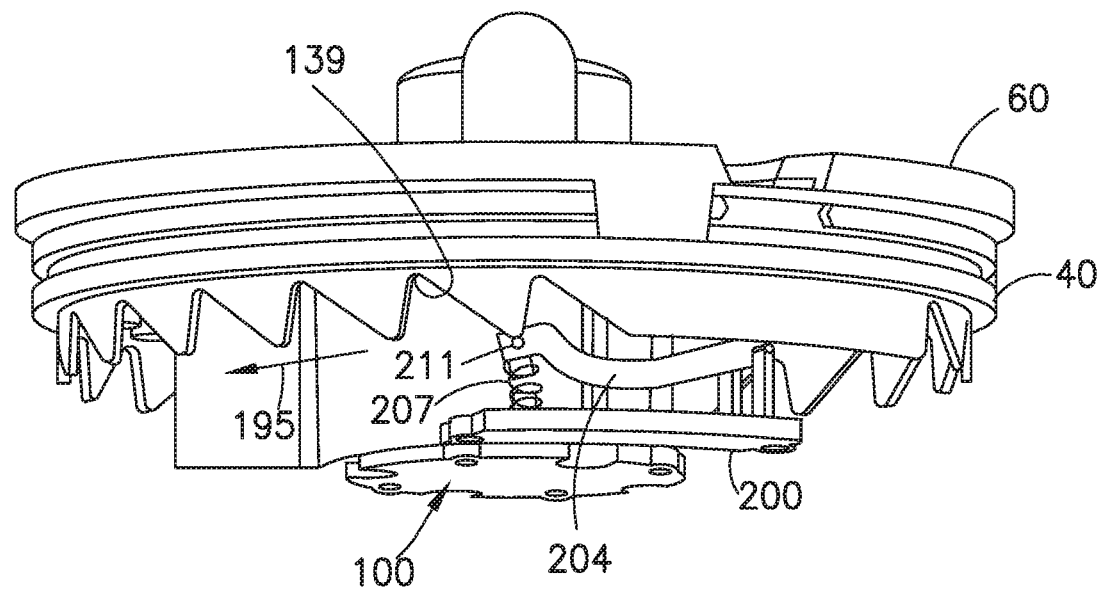
FIG. 18 is a bottom perspective view of the support shown the ejector mechanism.
Figure 19:
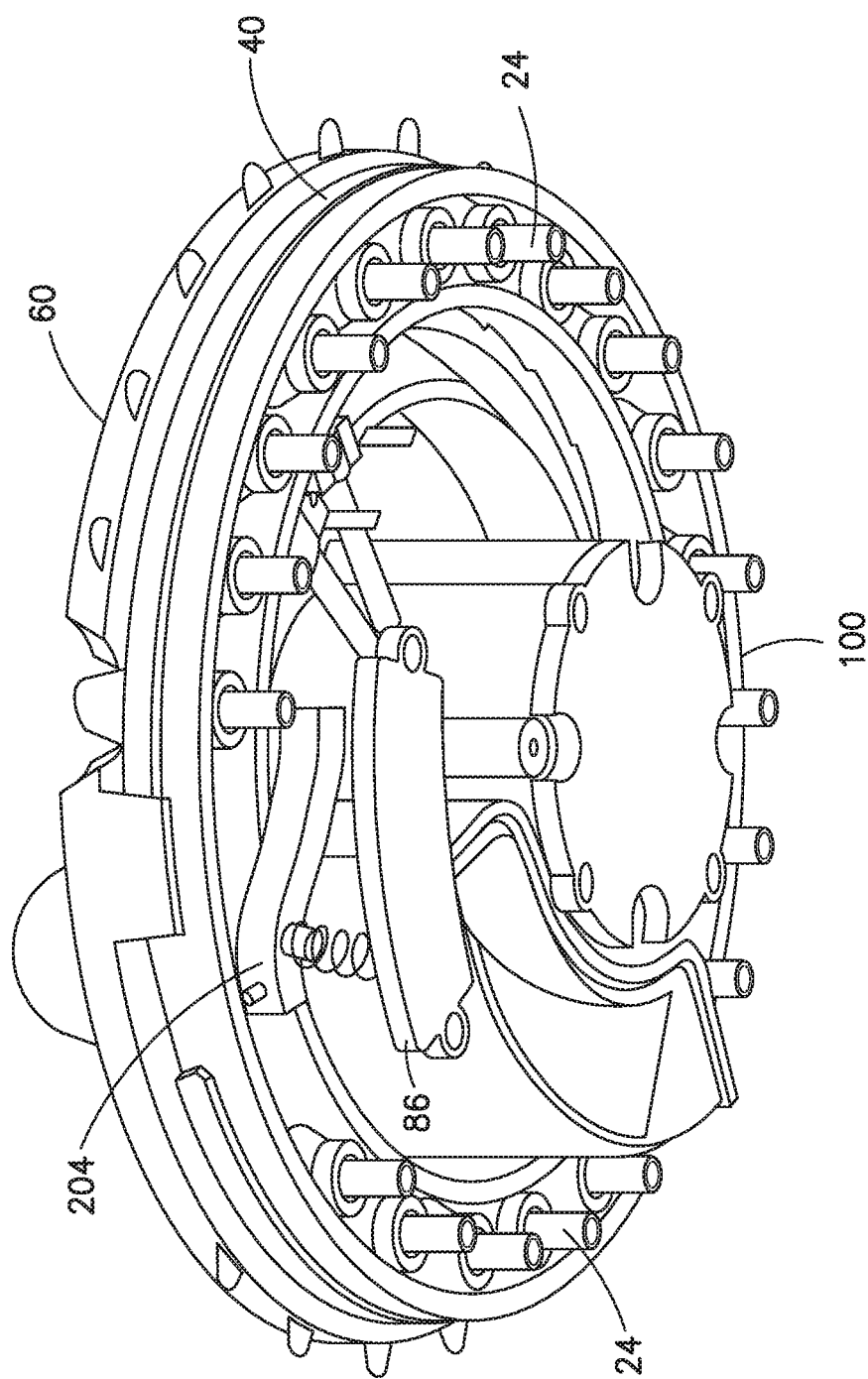
FIG. 19 is a bottom perspective view of the support showing the ejector mechanism.

The ejector 80 is spring biased to the position shown in FIG. 16. The distal end 208 is provided with a detent 211 shown as a pin projecting from the side of the arm 204. The detent 211 is positioned to engage the teeth 134 of the support 40 to move the arm in an up and down motion and to function as a ratchet to allow the support 40 to rotate in a forward direction and resist rotation in a reverse direction. Referring to FIG. 18, the detent 211 slides along the inclined surface 136 of the teeth 134 as the support 40 rotates relative to the ejector 80 and housing 30. As the support 40 rotates the detent 211 slides up the inclined surface 136 to the position shown in FIG. 18 to deflect the arm 204 away from the support 40 as a used pen needle is advanced from the opening 64 in the cover 60. FIG. 19 shows the ejector and ring 40 without the ratcheting teeth 134.

Figure 20:
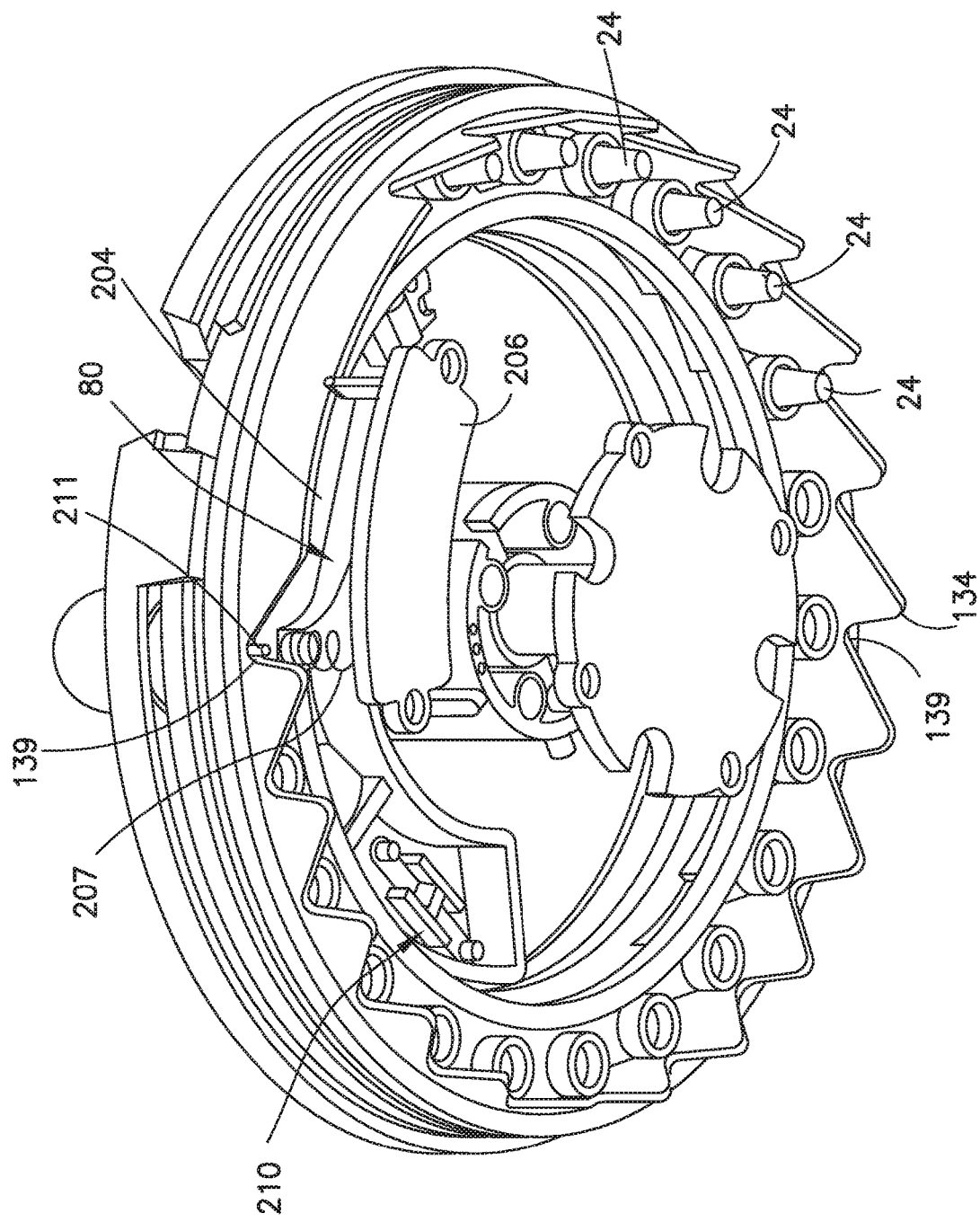
FIG. 20 is a top perspective view of the cover, support and ejector mechanism.

As shown in FIG. 20, the support 40 is advanced so that the detent 211 is spring biased into the trough 139 between the adjacent teeth 134. In one embodiment, the arm 204 snaps to the extended position shown in FIG. 20 by the spring 207 to strike the distal end of the pen needle projecting from the opening 46 in the bottom of the well 42 to eject the used pen needle in an upward direction into the recess 66 defined the dome 64 shown in FIG. 21 and FIG. 22. As the support 40 is again rotated to advance a new pen needle into position in the opening 64 in the cover 60, a used pen needle is advanced while the teeth 134 on the support 40 depress the ejector arm 204 to a loaded position against the biasing force of the spring 207.

As shown in the drawings, the actuator 56 is depressed to advance and index a pen needle 18 into view in the opening 64 in the cover 40 as shown in FIG. 3. The seal is removed so that the pen needle can then be connected to a pen delivery device for use. After use, the needle hub 16 is inserted back through the opening 64 into the outer cover 22 so that the delivery pen 10 can be disconnected by unscrewing and separating from the needle hub. Depressing the actuator 56 then advances the used pen needle so that distal end of the outer cover 22 is positioned with respect to the ejector 80 so that pen needle 18 is pushed upward into the recess 66 formed in the cover 60 and is directed into the compartment for the used pen needles.

As shown in FIGS. 21-24, housing 30, cover 30 and tray 74 cooperated to form an extractor mechanism 210 to assist in removing the inner shield 24 of the pen needle assembly without the need for the patient to handle the inner shield. The extractor 210 is provided for removing the inner shield 24 from the needle hub 16 prior to use and for disposal after use. The extractor 210 includes a gripping mechanism that is able to grip the inner shield so that the needle hub can be pulled free and where the used inner shield can be deposited into the tray 74 or other storage container for disposal.

Figure 21:
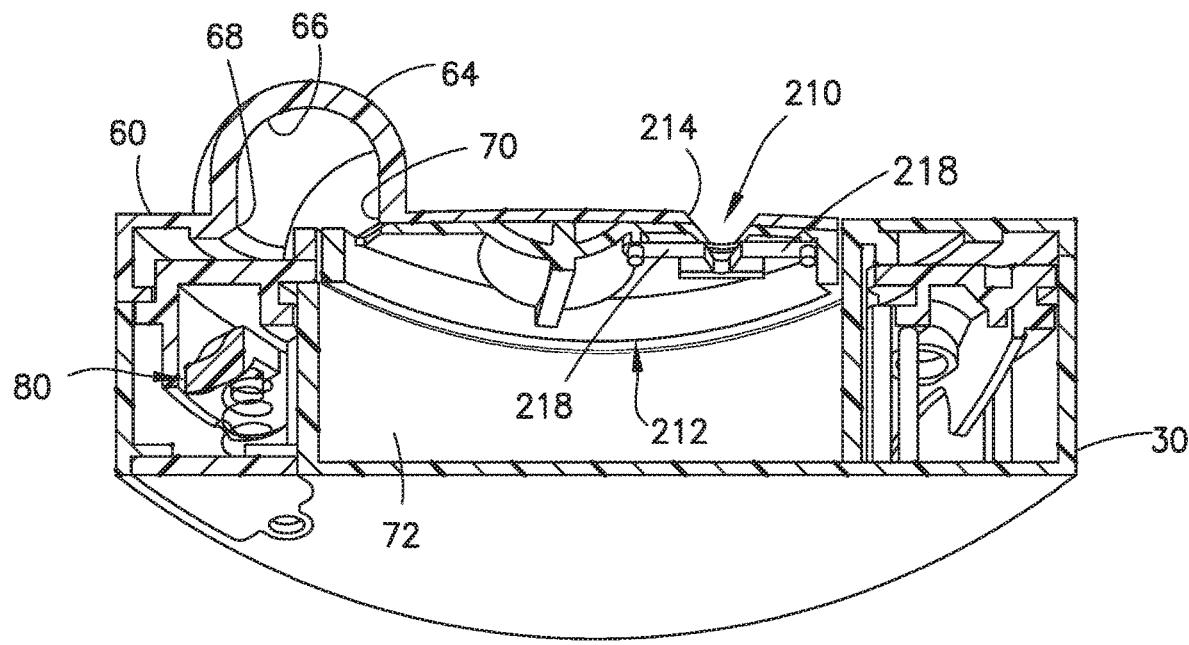
FIG. 21 is partial cross sectional view of the apparatus showing the inner shield extractor for the inner shield.

In the embodiment shown, the extractor 210 is coupled to the lid 212 of the tray 74 as shown in FIGS. 21-24. The cover 60 of the apparatus includes an opening 214 with a chamfered edge with a dimension configured for receiving the inner shield and preventing the needle hub from passing through the opening. The lid 212 and tray 74 are positioned in the apparatus below the opening 214 as shown in FIG. 21. The lid 212 includes an opening 216 with a chamfered edge on a top face and aligned with the opening 214 in the cover 60. The opening 216 in the lid and the opening 214 in the cover form a well for received the inner shield. The opening 216 also has a dimension configured for receiving the inner shield.

Figure 22:
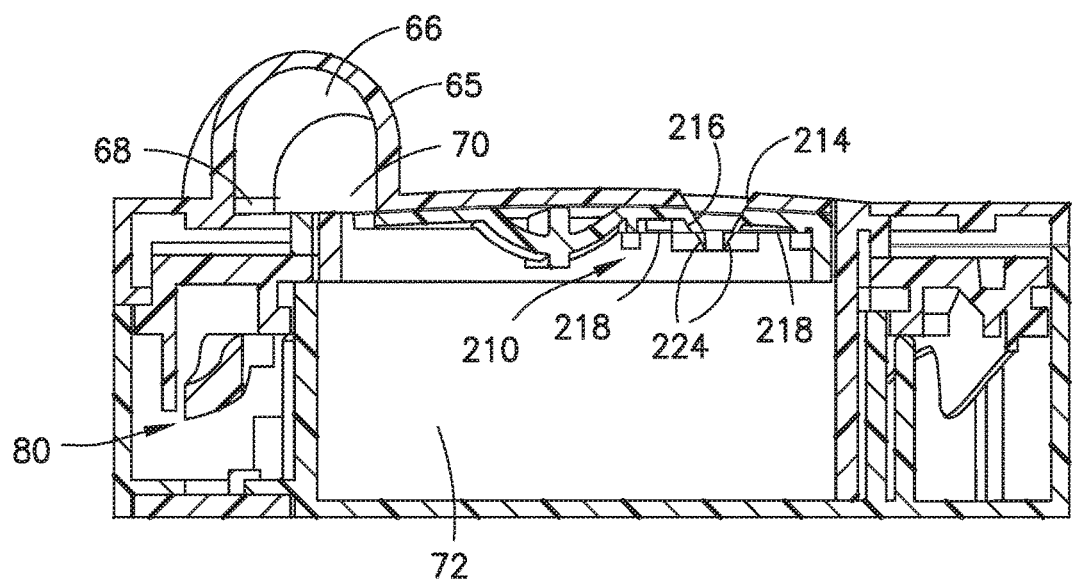
FIG. 22 is a cross sectional view of the apparatus showing the inner shield extractor.

In the embodiment shown, the extractor 210 includes gripping members shown as spring metal clips 218 mounted on the bottom face 220 of the lid 212 on opposite sides of the opening 216. Each clip 218 has a body 220 with an aperture 222 coupled to a respective post 221 on the bottom face the lid 212. A distal end of the clip 218 includes an angled tab 224 having an edge 226 projecting into the passage defined by the opening 216 as shown in FIGS. 21 and 22. In use, the inner shield 24 is inserted through the openings 214 and 216 where the edges 226 of the spring clips 218 grip the inner shield to resist removal of the inner shield in an outward direction relative to the cover 60 so that needle hub can be separated from the inner shield. The body 220 and/or the angled tabs 224 are sufficiently flexible to bend inwardly to allow transfer of the inner shield to the tray while resisting pulling the inner shield in an upward direction. An inner shield of a new pen needle can then be inserted through the opening to push the previous inner shield past the spring clips 218 to pass into the tray 74 so that the spring clips can grip the new inner shield for separation of the needle hub from the inner shield.

Figure 23:
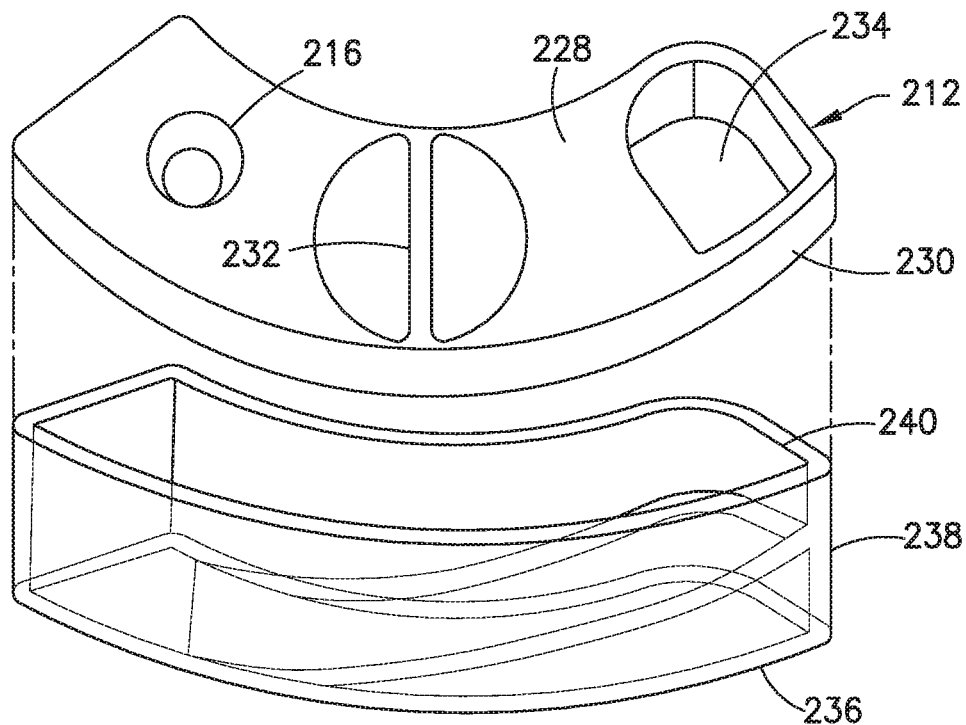
FIG. 23 is an exploded view of the tray and lid.
Figure 24:
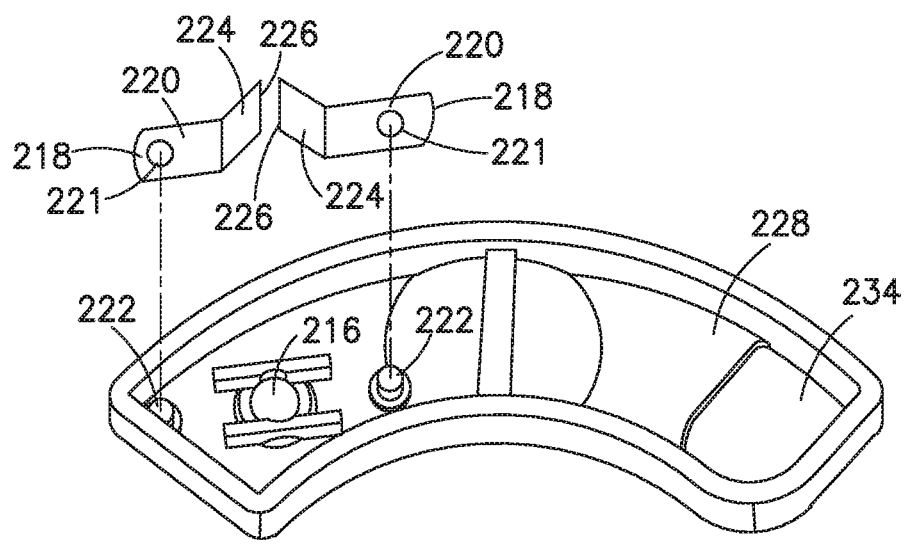
FIG. 24 is an exploded bottom perspective view of the lid and spring clips of the inner shield extractor.

In one embodiment, the tray 74 and lid 212 have a shape complementing the shape of the apparatus. As shown in FIG. 23, the tray and lid have a generally curved shape of the housing 30. The lid 212 has top wall 228 and a peripheral side wall 230. A molded handle 232 is formed in the top wall 228 to assist in separation from the tray. An opening 234 is provided for receiving the pen needles that are ejected from the wells through the passage 66 in the cover.

The tray 74 in the embodiment shown, has a bottom wall 236, a side wall 238 and an open top end 240 for mating with the lid 212. The bottom wall 236 can be formed with an inclined face to slope away from the opening 234 in the lid 212 to prevent the used pen needles from collecting directly below the opening.

The assembly is able to receive a pen needle assembly to assist the user in attaching the hub to the delivery pen without the need for the user to handle the needle hub and exposed cannula. During use, the actuator is depressed so that the support 40 and pen needle 18 are advanced to a position aligned with the opening 62 in the cover 60 where the pen needle is visible and accessible. The label is removed from the outer cover with the pen needle received in the well of the support 40.

A delivery pen is then inserted through the opening 64 in the cover of the housing to engage the needle hub of the pen needle. The delivery pen is rotated to engage the internal threads on the needle hub to couple to the delivery pen. The delivery pen with the attached needle hub 16 can be retracted from the outer cover leaving the outer cover retained in the well 42.

The inner shield 24 is attached to the needle hub to cover the cannula when separated from the outer cover. The inner shield of the pen needle is then inserted into the extractor 210 as shown in FIGS. 21-24 where inner shield 24 passes through the opening so that the edges 226 of the clips engage the outer surface of the inner shield to grip the inner shield and resist upward movement. The delivery pen can then be extracted leaving the inner shield 24 retained in the extractor.

After use of the delivery pen and the pen needle, the delivery pen can then be inserted through the opening 62 in the cover 60 where the needle hub is again received in outer cover 22 that is retained in the well 42, The delivery pen can then be rotated to disconnect the delivery pen from the internal threads of the needle hub and removed from the apparatus. The actuator 56 can then be depressed to rotate the support 40 to index the well 42 and the used pen needle toward the ejector 80. The movement of the support causes the spring biased arm 204 of the ejector to strike the distal end of the outer cover 22 to eject the pen needle upward and out of the well 42. The used pen needle 18 then passes through the passage defined by the recess 66 and into the tray 74 received in the compartment of the housing. The cover can be opened to remove the tray 74 for disposal of the used pen needles.

The foregoing embodiments and advantages are merely exemplary and are not to be construed as limiting the scope of the present invention. The description of an exemplary embodiment of the present invention is intended to be illustrative, and not to limit the scope of the present invention. Various modifications, alternatives, and variations will be apparent to those of ordinary skill in the art, and are intended to fall within the scope of the invention. It is particularly noted that the features of different embodiments and claims may be combined with each other as long as they do not contradict each other. Accordingly, all such modifications are intended to be included within the scope of this invention as defined in the appended claims and their equivalents.

The invention claimed is:
1. A pen needle assembly apparatus comprising:
a housing having an inner cavity, a top end, and a bottom end, and a support having a plurality of wells, each of said wells being configured for receiving a pen needle;
a cover coupled to said housing and having an opening for accessing at least one of said pen needles;
an actuator connected for moving said support to a position where said pen needles are sequentially indexed to a position for accessing the pen needle; and
a tray for receiving an inner shield of said pen needle, said tray having an extractor for gripping the inner shield during removal of the inner shield from the pen needle and directing the inner shield into the tray.

2. The pen needle assembly apparatus of claim 1, wherein said support is rotatable within said housing, and where said actuator is connected to said support to rotate said support to said position to access each of said pen needles through said opening in said cover.

3. The pen needle assembly apparatus of claim 2, wherein said actuator is movable in a linear direction, said actuator having a cam surface operatively connected to said support, whereby linear movement of said actuator rotates said support.

4. The pen needle assembly apparatus of claim 1, wherein said support includes a ratchet to rotate said support in a first direction and limit rotation of said support in a second direction.

5. The pen needle assembly apparatus of claim 4, wherein said support is configured to receive a used pen needle in said well after use of said pen needle, and where said apparatus includes an ejector proximate said opening in said cover where rotation of said support ejects the used pen needle from the well through a second opening.

6. The pen needle assembly apparatus of claim 5, wherein said ejector includes a spring biased arm to contact a used pen needle in the well by rotation of said support and to transfer an ejected pen needle into a compartment in the housing.

7. The pen needle assembly apparatus of claim 6, wherein said cover has a second opening oriented with respect to said ejector and communicating with said compartment for directing the ejected pen needle from said well into said compartment.

8. The pen needle assembly apparatus of claim 7, wherein said support has a plurality of teeth configured to engage said spring biased arm to compress said spring biased arm and to release said spring biased arm to strike a distal end of the used pen needle to eject the used pen needle from the respective well.

9. The pen needle assembly apparatus of claim 7, wherein said support includes a plurality of teeth configured for contacting said spring biased arm to move said spring biased arm to a loaded position and to release said spring biased arm to strike the used pen needle.

10. The pen needle assembly apparatus of claim 1, wherein the extractor comprises metal clips mounted on a bottom face of a lid of the tray and configured to grip the inner shield.

11. A pen needle assembly apparatus, comprising:
a housing having top end;
a rotatable support positioned in said housing, said support having a plurality of wells with a dimension for receiving a pen needle, the plurality of wells each having an open top end, an open bottom end, and a side wall, wherein when a pen needle is received in a respective well a distal part of the pen needle extends through the open bottom end;
a cover coupled to said top end of said housing, said cover having at least one opening for accessing a pen needle, where said support is rotated to sequentially index each said pen needle to a position for accessing said pen needle through said opening in said cover, and where said wells can receive a used pen needle after use; and
an ejector for pushing on the distal part of the used pen needle for ejecting a used pen needle from the open top end of a respective well into a compartment of said housing by rotation of said support relative to said ejector and housing.

12. The pen needle assembly apparatus of claim 11, wherein said ejector contacts the used pen needle received in the well by rotation of said support relative to said housing.

13. The pen needle assembly apparatus of claim 11, wherein said ejector includes a movable arm configured to contact the distal part of the pen needle received in the respective well by rotation of the support, and where said arm ejects the pen needle from the open top end of the well into the compartment of the housing.

14. The pen needle assembly apparatus of claim 11, wherein said cover has an open recessed area forming a passage aligned with said ejector to pass the ejected pen needle to the compartment.

15. The pen needle assembly apparatus of claim 11, further comprising an actuator to rotate said support relative to said housing and cover.

16. The pen needle assembly apparatus of claim 15, wherein said actuator has a ratchet operatively connected to said support to rotate said support in a first direction and prevent rotation is a second direction.

17. The pen needle assembly apparatus of claim 15, wherein said actuator is movable in a linear direction and includes a cam surface and a rotation member contacting said cam surface, and where said actuator is connected to said support to rotate said support by linear movement of said actuator.

18. The pen needle assembly apparatus of claim 11, wherein:
the ejector comprises a spring biased arm; and
the support has a plurality of teeth configured to engage the spring biased arm to compress the spring biased arm and to release the spring biased arm to strike the distal part of the used pen needle to eject the used pen needle from the respective well.

19. A method of coupling a pen needle to a delivery pen and uncoupling a used pen needle from the delivery pen, said method comprising:
providing a pen needle apparatus having a housing, a rotatable support, an actuator, a tray for receiving an inner shield of the pen needle, and a pen needle ejector, the support having a plurality of wells receiving a pen needle;
rotating the support to a position to access a pen needle and coupling the delivery pen to the pen needle;
inserting the pen needle into the tray, wherein the tray has an extractor for gripping the inner shield during removal of the inner shield from the pen needle and directing the inner shield into the tray;
removing the inner shield from the pen needle;
returning the used pen needle to the respective well in the support and uncoupling the used pen needle from the delivery pen; and
rotating the support to a position where the used pen needle is ejected from the well by the ejector into a compartment in the housing.

20. The method of claim 19, wherein the pen needle apparatus includes a cover on an open top end of the housing, the cover having at least one opening for accessing the pen needle, said method comprising rotating said support to orient the pen needle in a position relative to the opening in the cover to access the pen needle.

21. The method of claim 20, wherein said cover has a recess forming a passage oriented with respect to the ejector, the method comprising rotating the support relative to the ejector to eject the used pen needle through the passage to the compartment.

22. The method of claim 21, wherein said ejector includes a movable arm for engaging a distal end of the pen needle, the method comprising rotating the support to actuate the ejector to eject the used pen needle from the well into the compartment.

* * * * *